United States Patent [19]

Brewer

[11] Patent Number: 4,966,134
[45] Date of Patent: Oct. 30, 1990

[54] ANKLE PROTECTOR

[76] Inventor: Jeffrey L. Brewer, 2602 Sandia, Nacogdoches, Tex. 75961

[21] Appl. No.: 346,372

[22] Filed: Apr. 28, 1989

Related U.S. Application Data

[63] Continuation of Ser. No. 17,929, Feb. 24, 1987, abandoned.

[51] Int. Cl.$^5$ .............................. A61F 5/37; A61F 5/04
[52] U.S. Cl. ................................... 128/80 H; 128/882; 128/85
[58] Field of Search ...................... 128/153, 166, 80 H, 128/882, 892, 85, 87 R, 80 D, 80 R; 36/89; 2/22

[56] References Cited

U.S. PATENT DOCUMENTS

| | | | |
|---|---|---|---|
| 1,546,551 | 7/1925 | Petri | 128/80 H |
| 2,532,955 | 12/1950 | Shook | 2/22 |
| 2,656,834 | 10/1953 | Hatkoff | 128/80 H |
| 3,268,912 | 8/1966 | Whelan | 128/166 X |
| 3,416,156 | 12/1968 | Marvid | 2/22 |
| 3,674,023 | 7/1972 | Mann | 128/166 |
| 4,076,022 | 2/1978 | Walker | 128/153 X |
| 4,263,905 | 4/1981 | Couch, Jr. | 128/892 |
| 4,280,489 | 7/1981 | Johnson, Jr. | 128/166 X |
| 4,313,433 | 2/1982 | Cramer | 128/166 X |
| 4,323,058 | 4/1982 | Detty | 128/80 H |
| 4,378,793 | 4/1983 | Mauldin et al. | 128/166 X |
| 4,440,158 | 4/1984 | Shapiro | 128/166 X |
| 4,505,269 | 3/1985 | Davies et al. | 128/87 R |
| 4,510,927 | 4/1985 | Peters | 128/80 H |
| 4,517,968 | 5/1985 | Greene et al. | 128/166 X |
| 4,586,272 | 5/1986 | Forster | 128/75 X |
| 4,628,945 | 12/1986 | Johnson, Jr. | 128/80 H |
| 4,665,904 | 5/1987 | Lerman | 128/80 H |
| 4,729,370 | 3/1988 | Kallassy | 128/80 H |
| 4,753,229 | 6/1988 | Sutherland | 128/80 H |

Primary Examiner—Robert A. Hafer
Assistant Examiner—Kevin G. Kooney

[57] ABSTRACT

An ankle protector is disclosed comprising (i) a pair of supports each including a hard exterior shell and a conformable interior replaceable pad adapted to be fitted, pad facing the leg, onto the lower leg, confrontingly opposing medial and lateral side portions of the leg above and below the ankle malleoli, the support not extending inferiorly sufficiently to engage a surface on which the foot rests, the pad having a higher surface friction face confronting the leg, the support members being circumferentially bound to the leg above the ankle malleoli by (ii) inelastic positive fasteners acting in concert with the high friction surface of the pad to provide, when fitted, a secure mount on the limb, and (iii) an inelastic strap interconnecting said supports, when fitted, tensively, under the sole of the posterior part of the foot.

5 Claims, 5 Drawing Sheets

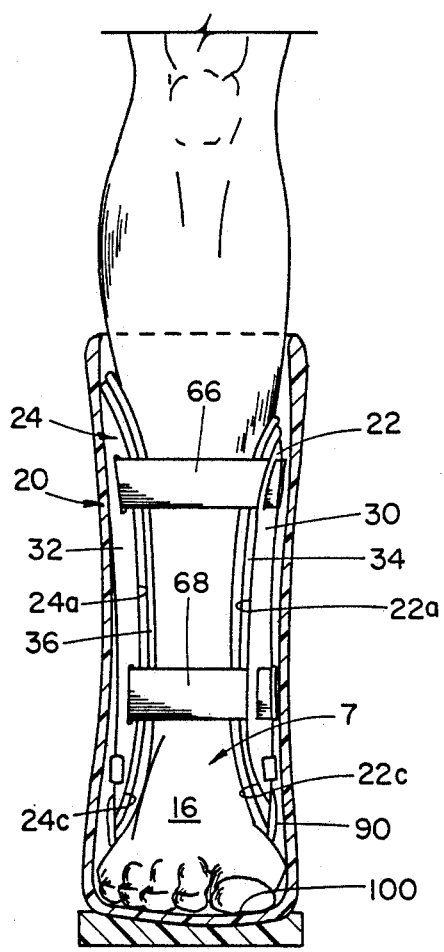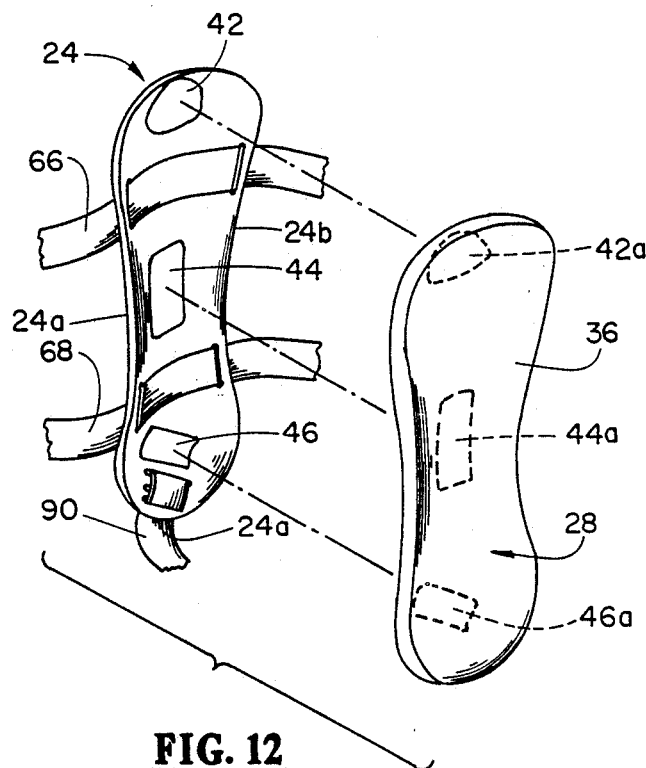
FIG. 12
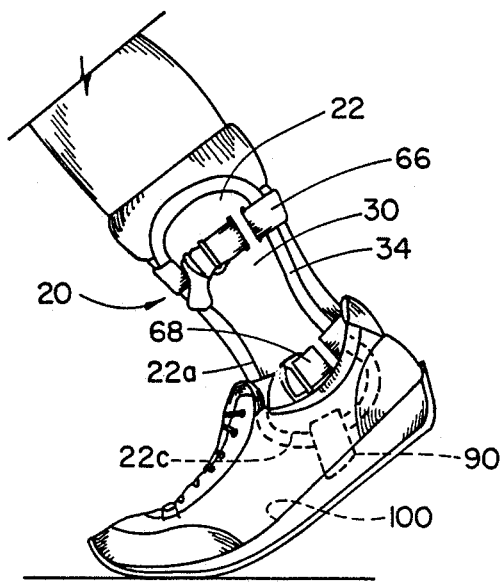
FIG. 13
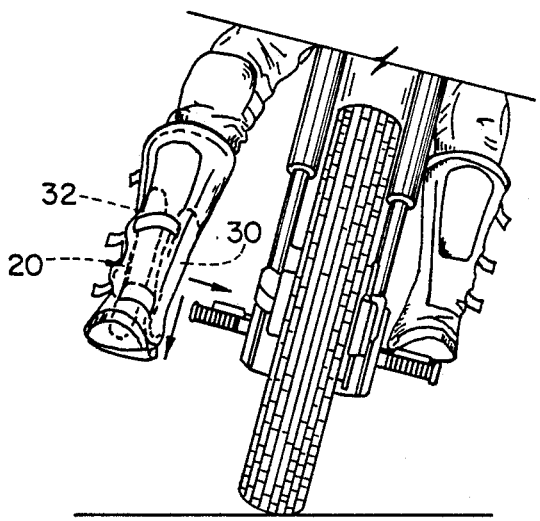
FIG. 14
FIG. 15

ANKLE PROTECTOR

This is a continuation of co-pending application Ser. No. 07/017,929 filed on Feb. 24, 1987 now abandoned.

BACKGROUND OF THE INVENTION

1. Field of the Invention.

This invention relates to orthotic protective devices for the ankle joint and in particular to devices which are meant to permit dorsiflexion and plantar-flexion of the foot while protecting against inversion or eversion of the foot.

2. Description of the Prior Art

The layman generally speaks of the ankle as the two prominent bony protuberances at the base of the lower leg. Referring to FIGS. 7-11, these protuberances are the expanded inferior or lower extremeties of the tibia 1, which is the large weight-bearing bone of the leg, and the fibula 2, a slender bone which lies parallel to the tibia and does not participate in weight-bearing. The tibia is nearer the medial plane of the body (a vertical plane through the erect body at the midline from behind to front), and is said to be "medial" to the fibula, which, conversely, is farther from the medial plane and is said to be "lateral" to the tibia. The two protuburances are called the medial malleolus 3 (tibia) and the lateral malleolus 4 (fibula). Anatomically the lower or distal end of the tibia rests on the ankle bone 5 called the talus, which in turn rests on the upper surface of the heel bone 6 called the calcaneous. The talus is held between the two malleoli, and with them and the lower end of the tibia, forms the ankle joint, indicated generally by the reference numeral 7.

The ankle joint 7 is of the hinge type, its form being that of a mortise and tenon, the box-like mortise being constructed superiorly by the distal surface 8 of the tibia, medially by the lateral aspect 9 of the medial malleolus 3, and laterally by the medial side 10 of the lateral malleolus 4. Posteriorly the socket between the tibia and fibula is completed by a ligament (the transverse tibiofibular ligament), not shown. The tenon of the joint is the upper articulating body 11 of the talus (the "trochlea").

Hinge movement at the ankle joint takes place around a transverse axis on a level with the tip of the lateral malleolus 4 and slightly below the level of the medial malleolus 3. In "dorsiflexion" the foot is drawn upwards, the trochlea 11 of the talus rotating backwards in the tibio-fibula socket; movement in the opposite direction is "plantar-flexion" (see FIG. 11). The trochlea narrows from front to back and is most snugly grasped between the malleoli in full dorsiflexion and least snugly held in full plantar-flexion.

The joint is surrounded by a joint capsule which, in correspondence with the requirements of free hinge movement at the ankle, is very weak in front and behind. The stability of the joint is given at the sides by the collateral ligaments. These are an exceedingly strong deltoid ligament 12 on the medial side radiating down from the medial malleolus 3 and, on the lateral side, are three separated ligaments originating from the lateral malleolus 4. The deltoid ligament on the medial side is so strong that the medial malleolus to which it is attached more commonly breaks than the ligament ruptures. On the lateral side, the three separate lateral ligaments (the anterior talofibular 13, the calcaneofibular 14, and the posterior talofibular 15) are much less strong connections than the deltoid ligament.

Because the joint ligaments are much weaker to the front and laterally, an ankle sprain is almost always due to an involuntary inversion or twisting of the foot inwardly, wrenching the trochlear of the talus outwardly in a lateral direction (often combined with a forward displacement), resulting in strain, tearing or rupture of one or more of the lateral ligaments (see FIG. 8). Far less common than inversion injury is ankle injury due to eversion or twisting of the foot outwardly, but impact or crush injury to the medial malleolus, such as caused by the footpegs of a motorcycle, can chip off a portion of the medial malleolus, tearing some of the deltoid ligament and, if the foot is everted strongly, also may fracture or break the lower part of the fibula. Either inversion or eversion injury, with displacement of the trochlear body, often pinches and mashes the synovial membrane of the ankle joint and rips associated vasculature, causing extensive swelling of the joint and foot due to fluid exudation. Once sprained, the ligaments seem never as strong as before, and the joint is more liable to a recurrence of the injury.

The time honored treatment of the sprained or fractured ankle is to immobilize it in a cast, usually split to avoid strangulation of the limb from the swelling. This fixes the joint to allow the ligaments and other injured tissues to mend. After a number of weeks the cast is removed and an orthotic device or aid usually is fitted or applied to permit recuperative walking with plantar-flexion and dorsiflexion while restricting inversion or eversion of the foot. This treatment and an orthotic device for that purpose is described in U.S. Pat. No. 4,280,489 issued to Johnson on July 28, 1981, marketed as the AIR-STIRRUP ankle brace by Aircast Incorporated, Summit, N.J. This device includes a U-shaped stirrup formed by a base to which are attached two vertical side members extending from the base to form sidewalls for a pair of air bags placed adjacent the lateral and medial sides of the leg and foot all the way to the stirrup base, with VELCRO closures being used to maintain the sidewalls and airbags against the sides of the legs. The device is worn in a laced shoe for effective resistance of inversion or eversion The patent describes forming the sidewalls with a thermoplastic material and contemplates replacing where the sidewalls neck down to join the base with a short flexible webbing to avoid fractures at the joinder caused by vigorous use. The marketed AIR-STIRRUP device attaches a loop backed web to VELCRO hook patches on the inside of the sidewalls and passes the web through a slot at the bottom of each sidewall then through the heel pad formed by a doubled-over VELCRO hook fabric to permit vertical down adjustability of the heel pad relative to the ankle recesses formed in the sidewalls.

Another type of orthotic device, exemplified by U.S. Pat. No. 4,510,927, issued to Peters on Apr. 16, 1985, and U.S. Pat. No. 4,517,968, issued to Greene et al on May 21, 1985, employs a rigid or semi-rigid heel cup or stirrup which supports uprights at a pivot mount proximate the transverse axis of rotation of the ankle joint. Foam pads are provided for comfort between the leg and the uprights and typically VELCRO closures or straps are used over the uprights for easy application.

The Peters patent contains an informative discussion of the prior art for orthotic ankle braces, to which reference is made. In addition to the devices described in the Peters patent, other devices allowing dorsiflexion and plantar-flexion which may be mentioned include U.S. Pat. No. 487,492 to Pugsley, issued Dec. 6, 1892, and U.S. Pat. No. 1,465,233 to Posner, issued Aug. 14, 1923, both disclosing an unitary ankle support open at the front and rear; U.S. Pat. No. 2,830,585 to Weiss, issued Apr. 15, 1958, and U.S. Pat. No. 4,440,158 to Shapiro, issued Apr. 3, 1984, each show lace-up ankle supports closed at the rear.

Because the once-sprained or fractured ankle is weaker after injury, and to prevent recurrent or initial sprains, some high schools and most college and professional teams in sports such as football or basketball prophylactically tape the ankle joint of each leg of every athlete before the athlete is allowed on the playing court or field. The tape wrap of the joint is intended to brace the joint against inversion or eversion. The practice of taping is expensive and, while endured, not especially liked. Skilled athletic trainers or similarly trained personnel are needed to perform the taping; their time with its expense and the time of the athletes is consumed to apply the tape and then take it off, before and after every athletic event, whether practice or game days. The tape obviously is not reusable, and in the aggregate, day in and day out, large quantities of not inexpensive tape are consumed. Repetitive applications and removal of the tape can and often does involve discomfort and skin irritation to the athlete. Dorsiflexion and plantar-flexion often are compromised. Moreover, taping is not wholly effective, because under practice or game conditions with intense perspiration and less vigorous movement of the limbs at the ankle joint during running, jumping and change of direction, the tape tends to loose its grip. The frequency of ankle injuries in sports even with taping is testimony enough to the limited efficacy of taping. Still, it has remained the only widespread prophylactic solution to the problem.

Particularly for the injured athlete seeking to get back into playing time, efforts have been made to use variations of the orthotic devices mentioned above to provide additional support, with or without taping. The more effective such orthotics generally are lace-up supports with lateral stays and stiffeners, sometimes to mid-calf length, over which the shoe is laced: sort of a legging or toeless and heel-less boot within a shoe. Devices of the foot-cup pivoting type generally are too cumbersome and mechanically restrictive for athletic use. The AIR-STIRRUP device has been tried but found unsatisfactory for athletic use (the VELCRO closures and straps give way and slip with use and wear; the lining of the airbag is a slick plastic surface which does not grip the athlete's sock or leg, especially when wet with perspiration; and fitted within a shoe, the deep sidewalls of the device engage the inside surface of the shoe sole and are lifted up and let down or pivot back and forth with movement of the foot in the shoe).

Even while tolerated, these supplemental devices generally are not favored by the athlete, because, depending on the device, they are ineffectual, bulky, uncomfortable, add tiring weight to the limbs, particularly the lace-ups when wetted with perspiration, and are perceived by the wearer as compromising and slowing athletic performance, costing the athlete an edge against his or her competitor. Moreover, the devices are relatively expensive.

SUMMARY OF THE INVENTION

It is an object of my invention to provide an ankle protector, over which an athletic shoe or boot can be worn, which, with ready ease and convenience, disposing with the need for application by skilled trainers, can be applied for prophylactic use directly by the athlete himself or herself, and which, when worn during the vigor of practice or competition, will provide protection against sprain, fracture or reinjury of the ankle caused by involuntary inversion or eversion of the foot, while permitting unrestricted dorsiflexion and plantar-flexion for competition level running and jumping.

It is an object of my invention to provide an ankle protector which may be worn prophylactically to provide not only protection from involuntary inversion and eversion but also to protect the malleoli of the athlete from blows and impact injury, such as from kick or equipment impact, for example, in motorcross competition from motorcycle footpeg strike.

It is an object of my invention to provide an ankle protector which not only relieves the labor and cost of taping ankles but also is relatively inexpensive, durable, and is inexpensively repairable or rebuildable, encouraging its use by athletic departments to enable its' principal prophylactic purpose.

It is an object of my invention to provide an ankle protector which is light-weight not bulky not water absorptive, is comfortable, and which is fit conformable, thereby encouraging its use by athletes to enable its' principal prophylactic purpose.

It is an object of my invention to provide an ankle protector which, effective for prophylactic and protective use in sporting activities, is as well useful in less vigorous rehabilitative wear by nonathletes.

My invention accomplishing these goals and objects may be briefly summarized as an ankle protector comprising a pair of substantially rigid, elongated and spaced apart support members adapted to fit against the lateral and medial surfaces of the lower limb above and below the malleoli, ending below the malleoli a distance sufficiently above the surface on which the relaxed foot rests to prevent engagement of the lower or inferior margin of the support member with such surface during movement of the foot (voluntary or involuntary dorsiflexion, plantar-flexion, inversion or eversion). The inside face of each support member is formed to have a high surface-friction. Inelastic positive or nonslip fastening means secure the slip-resistant support members to the lower leg. An inelastic strap is attached to the support members to be in tension under the posterior part of the bottom of the foot. The rigidity of the support members, the high surface-friction inside faces of the support members, the grip of the positive or nonslip fasteners on the surface members about the leg, and the cooperatively maintained tensed inelastic strap connecting the support members beneath the bottom of the foot, all combine to enable impartation of forces working on the foot that oppose forces tending to invert the foot (and strain the lateral ligaments) or evert the foot (and threaten the medial malleoli and medial ligaments). Preferably the support member comprises a substantially rigid external shell and a resiliently compressible high surface-friction internal pad, and more preferably, the pad is detachably affixed to the shell for easy replacement.

My invention and further advantages of it will be better understood by reference to the associated drawings and the detailed description of a preferred embodiment of the invention and the manner of using the embodiment set forth below. In that connection, it should be appreciated that the invention itself is defined by the claims, which are appended at the end hereto; the embodiment illustrated and hereinafter described is merely exemplary, no limitation to the scope of the invention being intended by its example, for my invention as claimed contemplates such alterations and modifications applying the principles of the invention as would occur to one skilled in the art to which this invention relates.

BRIEF DESCRIPTION OF THE DRAWINGS

FIG. 12 is in exploded perspective medial view of the lateral ankle protector viewed in FIGS. 1 and 3.

FIG. 13 is a frontal elevation of the ankle protector of FIG. 1 fitted on the right lower limb within a motor-cross boot depicted in vertical cross section.

FIG. 14 is a medial elevation of the ankle protector of FIG. 1 fitted on the right lower limb within a running shoe with hidden portions of the protector depicted in dashed outline.

FIG. 15 is a frontal elevation of the ankle protector of FIGS. 1 and 13 depicted in dashed outline to illustrate a function of the protector.

DESCRIPTION OF THE PREFERRED EMBODIMENT

Figure 1:
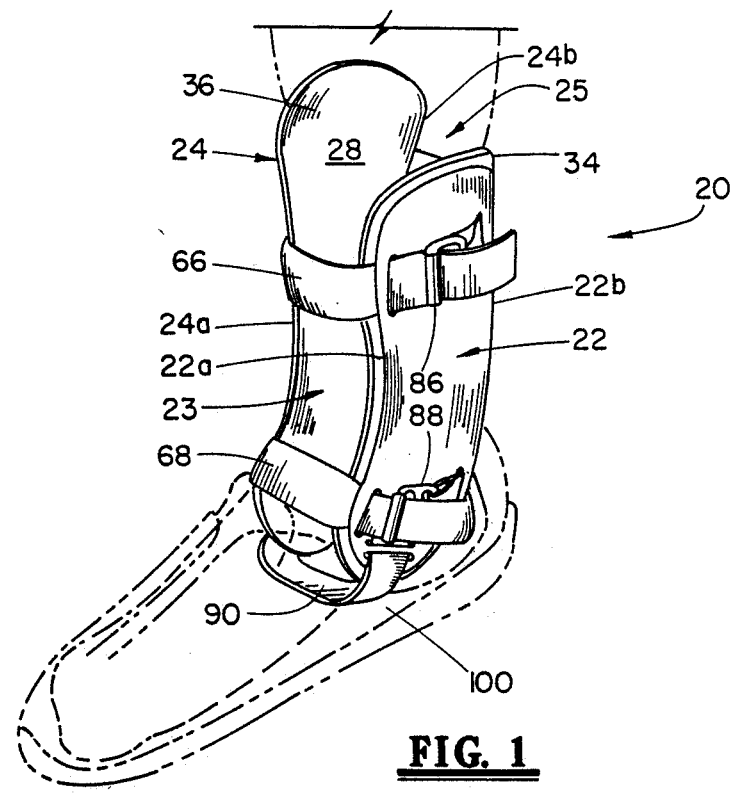
FIG. 1 is a perspective of the ankle protector of my invention viewed from the medial side showing the protector fitted on a right lower leg and foot within a running shoe depicted in dashed outline.

Referring to the drawings there is shown a preferred embodiment of an ankle protector constructed in accordance with my invention, represented generally by the reference numeral 20. Ankle protector 20 is depicted in FIGS. 1, 7, 10-11, 13-15 fitted on the right lower limb inclusive of the inferior portion of the lower leg and the posterior portion of the foot.

Referring to FIG. 1, ankle protector 20 comprises an elongate medial support member 22 and an elongate lateral support member 24, the respective inside faces 26 and 28 of which oppose, respectively, the medial and lateral side portions of the lower limb above and below the malleoli 3, 4 of the lower limb (FIGS. 9, 10, 11, and 13). The anterior margins 22a, 24a and posterior margins 22b, 24b of respective support members 22, 24 define an anterior opening 23 at the anterior of the lower limb and a posterior opening 25 at the posterior of the lower limb for unrestricted dorsiflexion and plantarflexion of the foot (FIG. 1).

The support members 22, 24 each comprise an outer shell 30, 32, respectively, and an inner pad 34, 36, respectively. The margins of the pads 34, 36 are substantially coextensive with the margins of the shells 30, 32 and as illustrated preferably extend slightly beyond the margins of the shells to provide cushion against any edge bite of the shell margins.

The substantially rigid shells 30, 32 preferably are formed of an injection molded high impact thermoplastic such as high impact polypropylene or polyurethane.

The respective inferior margins 22c, 24c of each shell 30, 32 extend below the malleoli 3, 4 of the lower limb a distance sufficiently above the surface 100 on which the relaxed foot 16 rests (FIGS. 1, 7, 9, 13, 14) to prevent engagement of the inferior margins 22c, 24c with the surface 100 upon movement of the foot, whether dorsiflexion, plantar-flexion (FIGS. 11, 14), inversion or eversion. Suitably the inferior margin 22c, 24c does not extend more than about midway between the malleoli 3, 4 and the surface 100 on which the relaxed foot reposes (reference here to the malleoli means the distal extremity of each malleolus 3, 4; see, for example, FIG. 9). Normally surface 100 will be the inner surface of the sole or base of the shoe or boot in which the foot is inserted (FIGS. 1, 13, 14).

The pads 34, 36 are resiliently compressible high surface-friction pads preferably formed of a flexible closed-cell polymer foam. I have found VOLARA Type A crosslinked polyethylene foam available from Voltek, Inc., Lawrence, MA. 01843 to be suitable, at a density of 2 lbs/cu.ft., for forming the pads. This material has low water absorption (0.04 lb/sq. ft. of cut surface, max, by ASTM D-1667) so that when worn it does not become heavy with perspiration; it has surface friction qualities effective for a sufficient nonslip engagement with an athletic sock or the skin (even when the sock is soaked or the skin is wet with perspiration), and is adequately compressible and resilient to provide fit conformability and comfort to the wearer (compressive strength in psi by ASTM D-1056 is 4.9–6.1 at 25% deflection, 12.7–15.5 at 50% deflection and 38.8–47.4 at 75% deflection, with compression set as a percent of original thickness after 22 hours loading and 24 hours recovery by ASTM D-1056 at 16 max).

Figure 3:
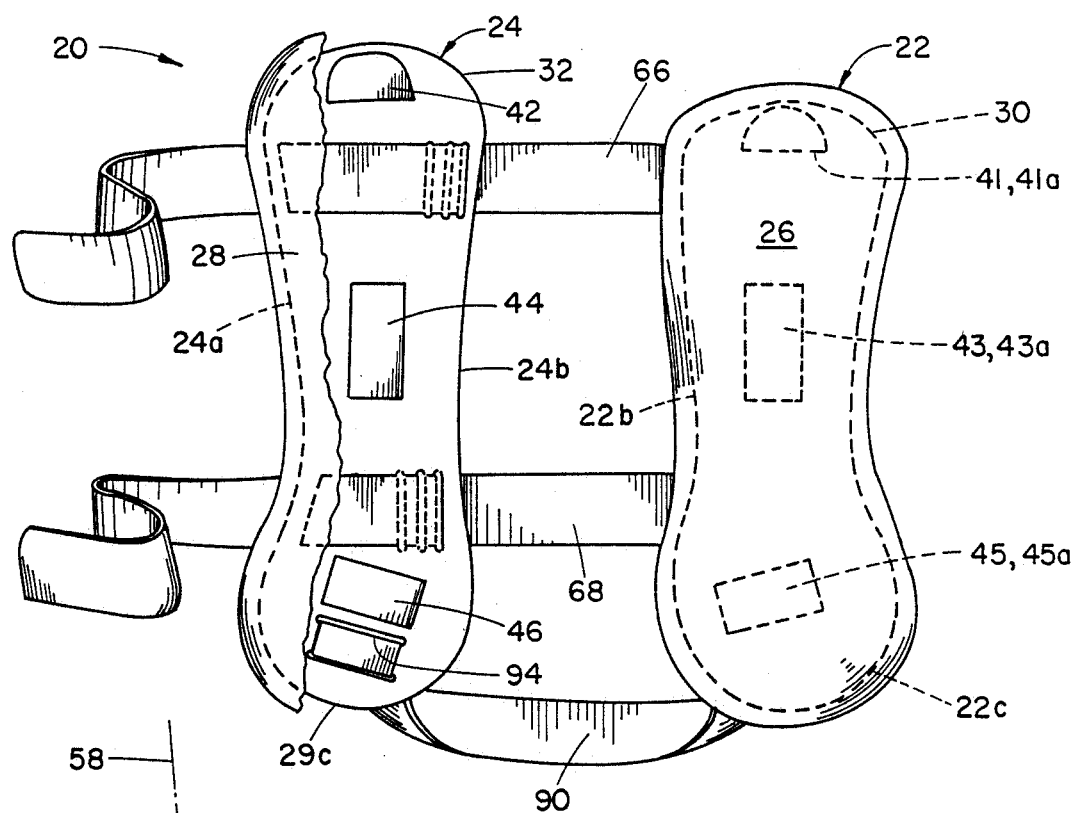
FIG. 3 is an elevation of the ankle protector of FIG. 1 spread and viewed from the front (as it is fitted to the foot) to illustrate the inside of the protector, with a portion broken away to reveal certain features depicted beneath by dashed line.

Referring to FIGS. 3 and 12, the pads 34, 36 preferably are removably affixed to shells 30, 32 suitably by VELCRO type hook fastener patches 41, 43, 45 and 42, 44, 46 glued or bonded respectively to the interior or back faces of shell 30 and shell 32 to fastenably engage respectively the VELCRO loop material patches 41a, 43a, 45a, and 42a, 44a, 46a, glued or bonded to the opposing interior or back faces of pads 34, 36 respectively.

Figure 2:
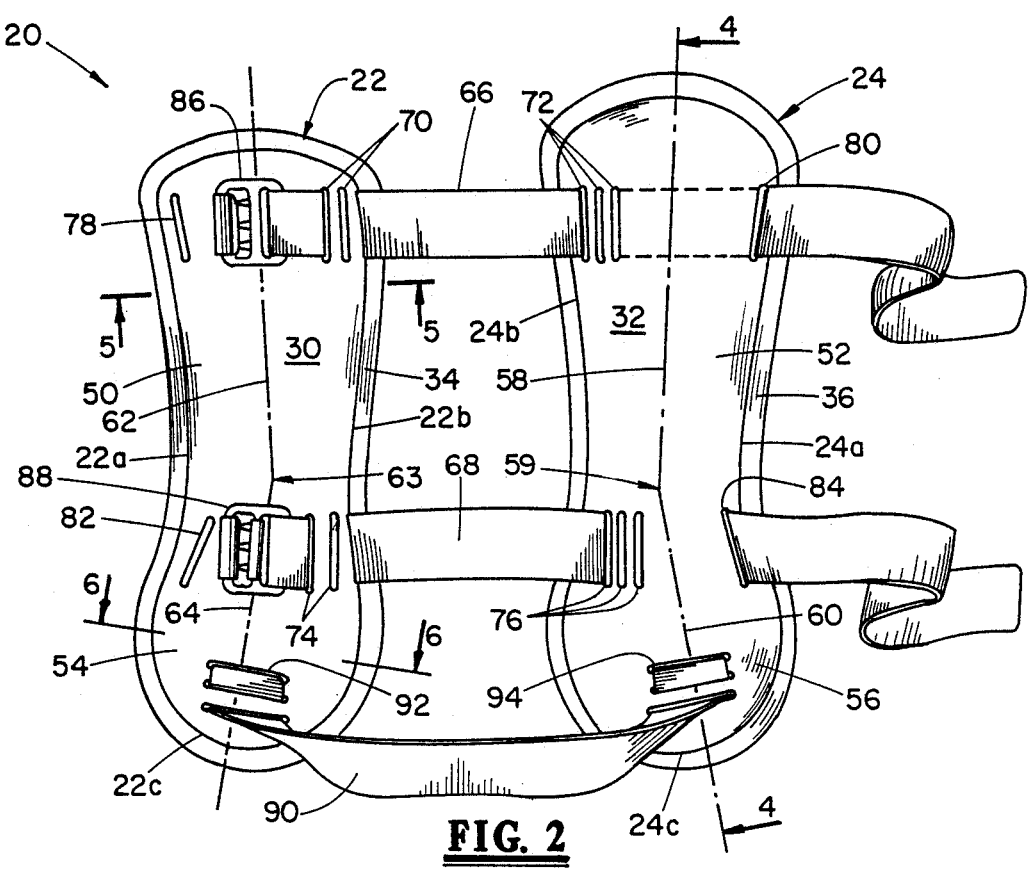
FIG. 2 is an elevation of the ankle protector of FIG. 1 spread and viewed from the rear (as it is fitted to the foot) to illustrate the outside of the protector.
Figure 4:
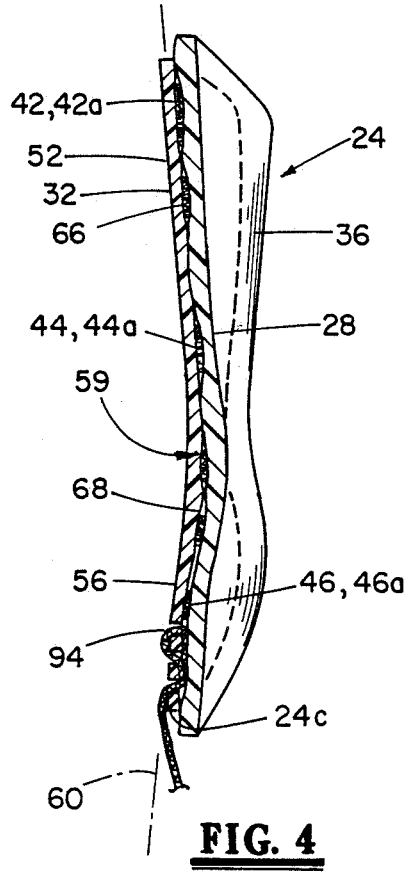
FIG. 4 is a vertical section of the lateral protector of FIG. 1 taken along the view direction of line 4—4 of FIG. 2.
Figure 5:
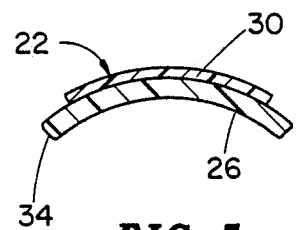
FIG. 5 is a transverse section of the lateral protector of FIG. 1 taken along the view direction of line 5—5 of FIG. 2.
Figure 6:
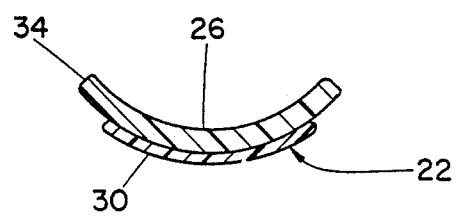
FIG. 6 is a transverse section of the lateral protector of FIG. 1 taken along the view direction of line 6—6 of FIG. 2.
Figure 9:
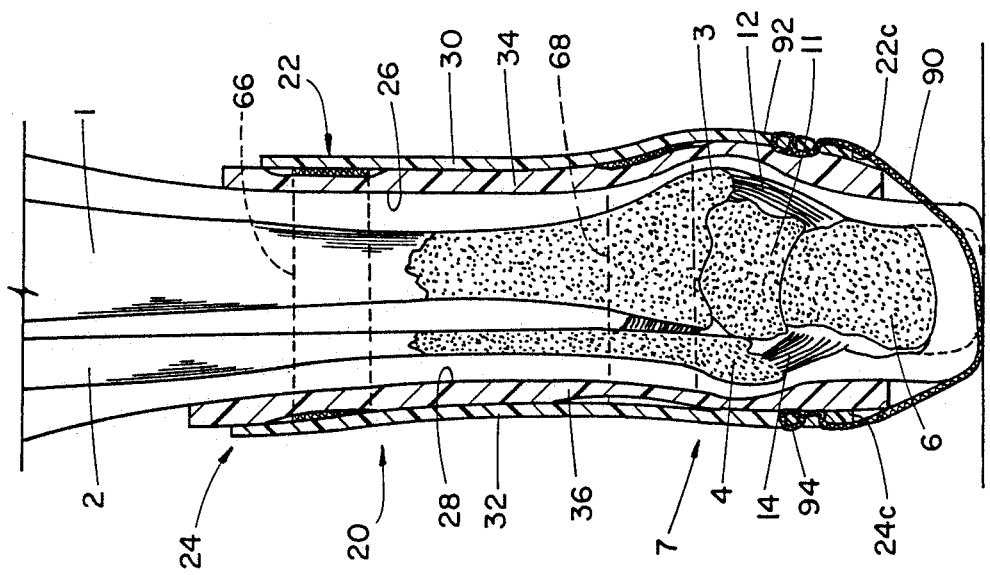
FIG. 9 is a schematic vertical section taken along the view direction of line 9—9 of FIG. 7, depicting in section the ankle protector of FIG. 1 fitted on the foot.
Figure 8:
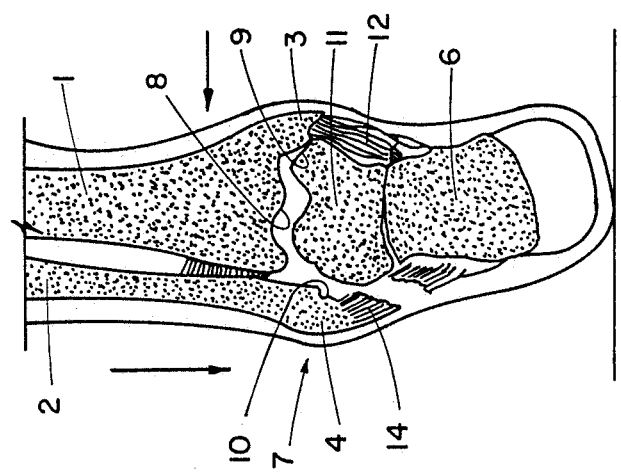
FIG. 8 is a schematic vertical sectional front view of a right foot and leg from the same directional line as at line 9—9 of FIG. 7.
Figure 7:
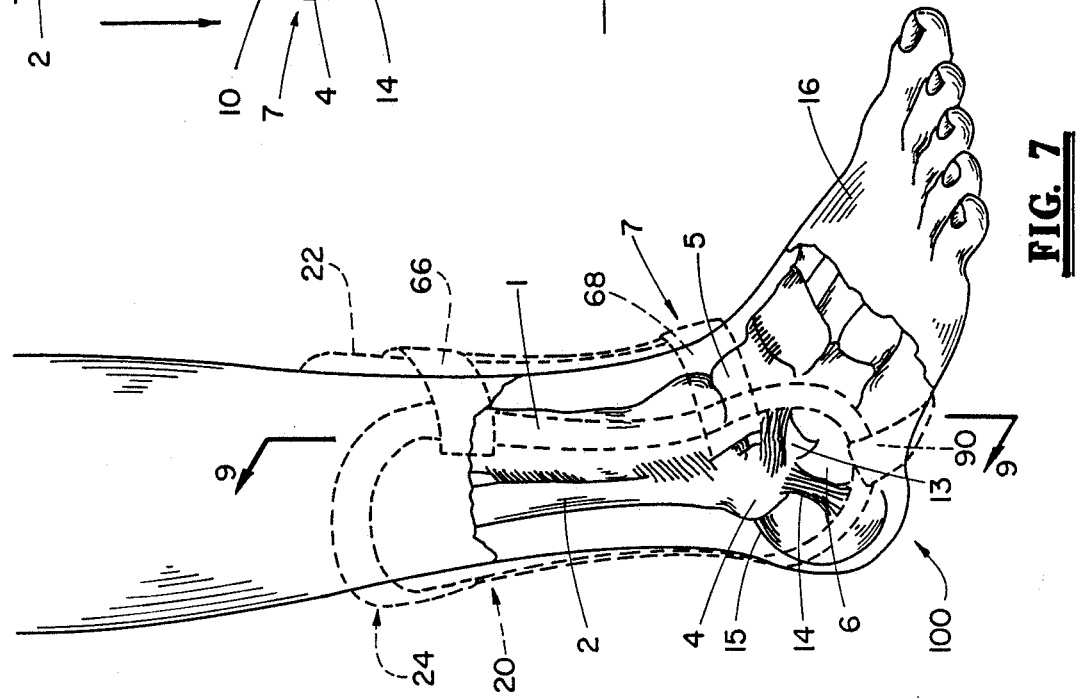
FIG. 7 is a schematic perspective lateral view of a right lower leg and foot with portions removed to depict certain bones and ligaments of the ankle over which is fitted the subject ankle protector shown in dashed outline.
Figure 10:
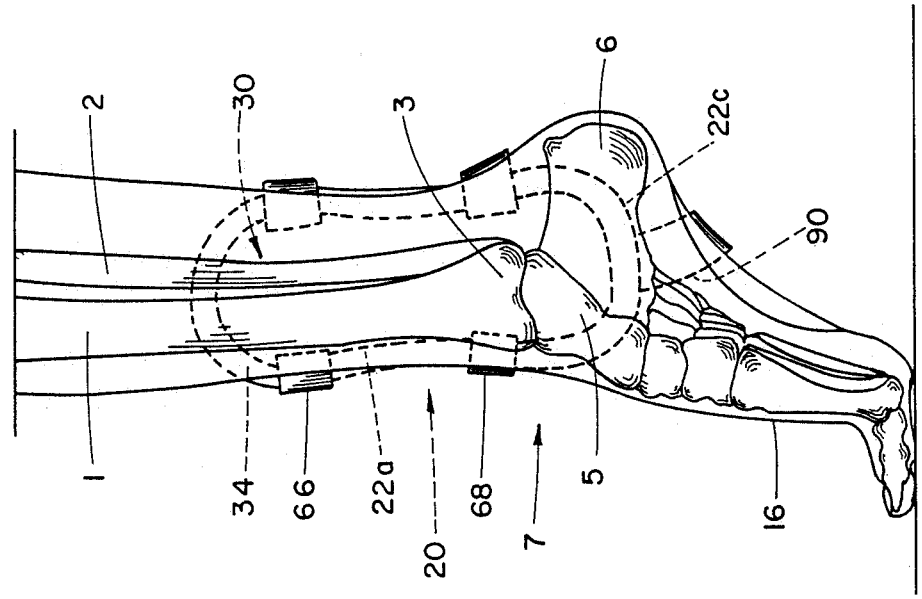
FIG. 10 is a medial schematic elevational view of a relaxed right lower leg and foot depicting skeletal members as in a radiographic tracing, showing the medial ankle protector of FIG. 1 fitted in dashed outline.
Figure 11:
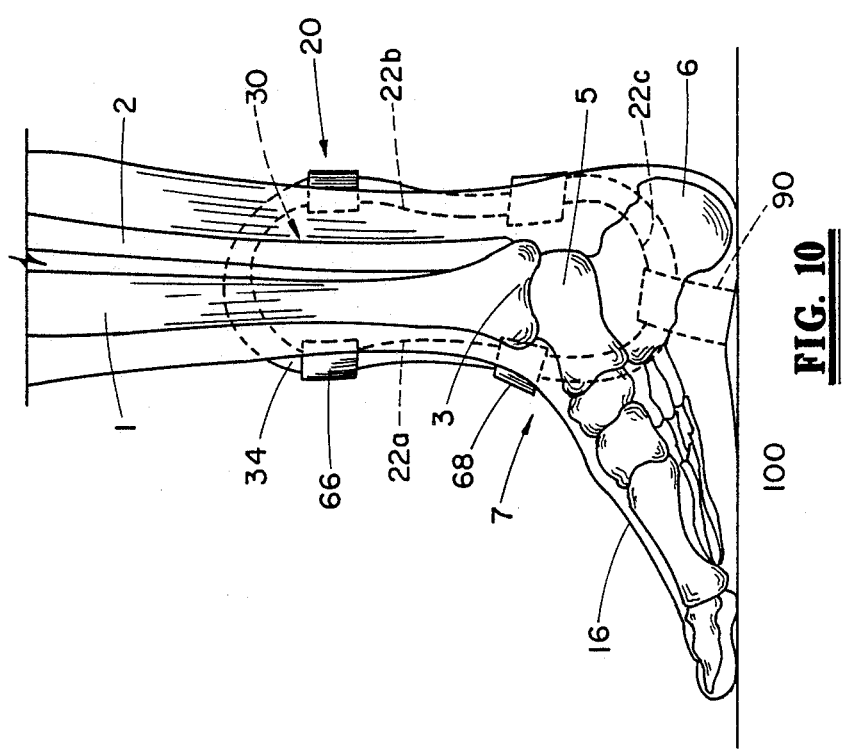
FIG. 11 is a medial schematic elevational view of a plantar-flexed right lower leg and foot depicting skeletal members as in a radiographic tracing, showing the medial protector of FIG. 1 fitted in dashed outline.

Referring particularly to FIGS. 2, 4, 5 and 6, shells 30, 32 of support members 22, 24 each are transversely arcuate (FIGS. 5 and 6) and comprise an upper portion 50, 52, respectively (FIGS. 2, 4, 5), and a lower portion 54, 56, respectively (FIGS. 2, 4, 6). Referring to lateral shell 32 the arcuate upper portion 52 of lateral shell 32 has a first longitudinal axis 58 and the arcuate lower portion 56 of lateral shell 32 has a second longitudinal axis 60. These axes 58, 60 intersect at 59 (FIGS. 2, 4) in an anterior-posterior direction (in the plane of the paper for FIG. 2, normal to the plane of the paper for FIG. 4), inclining anteriorly each to the other at an obtuse angle which points posteriorly. Suitably the posterior pointing angle of intersection of axes 58, 60 is about 167 degrees. Axes 58 and 60 also preferably incline to each other and intersect in a lateral direction (in a plane normal to the paper for FIG. 2, and in the plane of the paper for FIG. 4), also at a predetermined obtuse angle, this one pointing medially or inwardly (inwardly normal to the paper, FIG. 2; in the plane of the paper, FIG. 4). Suitably the medially pointed angle of intersection of axes 58, 60 is about 168 degrees. Similarly, medial support member 22 also has first and second longitudinal axes 62, 64 intersecting at 63 at anterior-posteriorly directed and at inwardly or medially directed and similar obtuse angles, suitably 167 degrees of or the posterior pointing angle and 168 degrees for the lateral angle. It has been found that these compound angles and shaping of the shells furnish suitable wearer comfort over the malleoli, nonslip anchoring of the support members relative to the malleoli, and prevent pinching interference with the foot skin overlying the calcaneous by inferior margins 22c, 24c.

Support members 22,, 24 when fitted opposingly about the confronted medial and lateral side portions of the lower limb are securedly attached onto the leg by inelastic positive fasteners, preferably a plurality of straps of cotton webbing 66, 68 coursing around the leg across and through one of plurality of locating adjustment slots 70, 72 or 74, 76 formed in the upper portions 50,52 and lower portions 54, 56 of shells 30, 32, and then through upper cinching slots 78,80 of upper portions 50, 52 and lower cinching slots 82, 845 of lower portions 54, 56, for buckling by flat safety locking webbing buckles 86,88, which provide exact adjustable and positive fastening of the straps about the leg. Suitably only one of slots 70, 72 or one of slots 74, 76 may be used. D-ring fasteners have been found not to provide a reliable non-slip or positive grip for the straps. The positive fastening straps and buckles act in concert on the leg with the high surface-friction of the inside faces 26, 28 of the support members 22, 24 to enable nonslip mount. Preferably as is illustrated, the positive or nonslip strap and buckle fasteners are located both above and below the intersections 59, 63 for better gripping.

Attached to support members 22, 24 at shells 30, 32, suitably at upper portions 50, 52, preferably at lower portions 54, 56 below the malleoli opposing portions, is an inelastic strap 90 adapted to be fitted under the posterior part of the sole of the foot in tension between the support members 22, 24 when the support members 22, 24 are in secured mount on the lower limb. Strap 90 is adjustably anchored to support member shells 30, 32 by weaving it through ladder slots 92, 94, illustrated in lower portions 54, 56.

For use, the athlete or other user places hist foot with heel against strap 90, brings medial and lateral support members 22, 24, interconnected posteriorly by straps 66, 68, in opposition respectively against the medial and lateral lower portions of his or her leg over his or her malleoli; if necessary for more comfortable fit, adjusts straps 66, 68 through another of the adjusting slots 70, 72 or 74, 76; laces the free end of straps 66, 68 through cinching slots 78, 82; inserts the said free ends through safety buckles 86, 88; and then pushes the buckle points through the webbing fabric to fix the strap cinch set.

Correctly adjusted, strap 90 should be in tight tension when the user stands, and an attempted voluntary abducting and twisting of the foot to raise the medial border and depress the lateral border until the sole is turned medially (voluntary inversion) will be resisted by strap 90, secured to the nonslip mounted support means 22, 24. Attempted voluntary inversion also will draw lower portion 56 of lateral shell 32 into closer lateral approximation with lateral malleolus 4 and over lateral ligaments, further to support against inversion. Protection against eversion works similarly. If heel strap 90 is slack and not in tension upon standing, the span of strap 90 bridging the lowest of the ladder slots 92, 94 is adjusted to remove the slack by drawing of the more webbing up through the remainder of the slots.

Fitted to the user, the limited reach of the inferior margins 22c, 24c of support members 22, 24 below malleoli 3, 4 prevents engagement of the margins 22c, 24c with the inside sole surface of the shoe which would disrupt the nonslip mount of the support members 22, 24 and consequently interfere with the tension forces on strap 90 which resist involuntary or voluntary inversion or eversion.

The fitted ankle protector 20 allows unrestricted dorsiflexion and plantar-flexion, strongly resists inversion and eversion in vigorous athletic play, and provides malleoli and collateral ligament protection from blows. For example, as illustrated in FIG. 15, either a shearing strike to the medial malleolus, depicted by the down pointing arrow, or a crushing blow to the malleolus, depicted by the medially pointing arrow, is protected against by the high impact thermoplastic shell 30, while involuntary inversion or everions twisting of the foot as the rider vertically impacts against the motorcycle pegs during violent motorcross maneuvers is guarded against by the functional operation of the ankle protector.

Ankle protector 20 is fittable by the athlete or other user himself or herself, provides a feasible alternative to universal taping of athlete ankles, is fabricated of lightweight durable materials, is reusable over and over, is modular for rebuildability, and has removable fit-conformable pads which may be laundered or replaced.

While the construction of the preferred embodiment of my invention has been described with particular fasteners, attachments and materials, variations and modifications within the spirit and scope of the invention will be readily apparent to those skilled in the art and are comprehended within the claims, which now follow.

I claim:

1. A brace for the ankle joint of a lower leg and foot of a person, comprising:
   first and second elongate support members having anterior, posterior, superior and inferior margins and adapted to receive respectively the lateral and medial aspects of the leg of a person, each member having a transversely arcuate inner face and an upper and a lower portion, first and second high surface friction resiliently compressible pad members substantially co-extensive respectively with said first and second support members and detachably affixable to the inner face of such first and second support members, respectively, means on the inner faces of said support members, cooperative with means on said resilient pad members, for detachably affixing said first and second pad members to said first and second support members, respectively, each said upper and lower portion having a longitudinal axis inclined laterally and anteriorly a minor degree from normal, said axes intersecting such that such intersection defines laterally- and anteriorly-included major obtuse angles of substantially similar obtuse degree, the axial distance from said intersection to said inferior margin of each said lower portion being smaller than the axial distance from said intersection to said superior margin of said upper portion, each said lower portion including, proximate the inferior margin thereof, means for fixing a heel strap thereat, each said lower portion further including, between said intersection and said heel strap fixing means, means for attaching ankle strap and fastening means, each said upper portion including remote from said intersection and between said intersection and said superior margin, means for attaching a leg strap and fastening means, a flexible, inelastic heel strap adjustably fixed to said heel strap fixing means for inferiorly interconnecting the lower portions of said first and second support members at the inferior margins thereof, for tensioned contact with the heel when said lower leg is received, such that such heel strap conforms snugly to the curvature of the sole of the heel, a flexible, in elastic adjustable ankle strap and fastening means attached to said lower portion attaching means and interconnecting the lower portions of said first and second support members, anteriorly, substantially transversely to said longitudinal axis of said lower portion, and, posteriorly, substantially transversely to normal, for tensioning said lower portions and said pad members onto said lower leg proximate said malleoli firmly snugly against said malleoli when said lower leg is received, and a flexible, inelastic adjustable leg strap and fastening means attached to said upper portions attaching means and interconnecting the upper portions of said first and second support members, anteriorly, substantially transversely to said longitudinal axis of said upper portion, and, posteriorly, substantially transversely to normal, for tensioning said upper portions and said pad member onto said lower leg distally above said intersection when said lower leg is received, to stabilize said first and second members above the ankle joint.

2. The ankle brace of claim 1 in which said means for attaching said ankle strap and fastening means comprises at least one anterior slot substantially adjacent the anterior margin of said support member lower portion and at least one posterior slot substantially adjacent the posterior margin of said support member lower portion, and said means for attaching said leg strap and fastening means comprises at least one anterior slot substantially adjacent the anterior margin of said support member upper portion and at least one posterior slot substantially adjacent the posterior margin of said support member upper portion.

3. The ankle brace of claim 2 in which said lower portion anterior slot is substantially parallel to said longitudinal axis of said lower portion and said upper portion anterior slot is substantially parallel to said longitudinal axis of said upper portion.

4. The ankle brace of claim 3 in which said at least one lower portion posterior slot is substantially parallel to normal and at least one upper portion posterior slot is substantially parallel to normal.

5. The ankle brace of claim 2 comprising a plurality of said posterior slots.

* * * * *